United States Patent [19]

Schiferl

[11] Patent Number: 5,059,369
[45] Date of Patent: Oct. 22, 1991

[54] REFRACTORY FIBER MODULE RETAINER SYSTEM

[75] Inventor: Joseph J. Schiferl, Johnson Creek, Wis.

[73] Assignee: General Signal Corporation, Stamford, Conn.

[21] Appl. No.: 860,702

[22] Filed: May 5, 1986

Related U.S. Application Data

[60] Division of Ser. No. 320,388, Nov. 12, 1981, abandoned, and a continuation of Ser. No. 634,739, Jul. 26, 1984, abandoned.

[51] Int. Cl.$^5$ .............................................. C04B 33/28
[52] U.S. Cl. ....................................... 264/87; 264/278; 264/273
[58] Field of Search .......................... 264/278, 87, 273

[56] References Cited

U.S. PATENT DOCUMENTS

| | | | |
|---|---|---|---|
| 2,341,777 | 2/1944 | Hensel | 52/509 |
| 3,499,066 | 3/1970 | Murray | 264/278 |
| 4,067,946 | 1/1978 | Rickert | 264/278 |
| 4,157,001 | 6/1979 | Pickles | 52/410 |
| 4,379,382 | 4/1983 | Sauder | 52/506 |

*Primary Examiner*—James Derrington
*Attorney, Agent, or Firm*—Robert R. Hubbard; John F. Ohlandt

[57] ABSTRACT

A refractory fiber module retainer system and a method of forming such retainer system is disclosed; the system includes a unitary refractory fiber module possessing substantial rigidity; the module being formed, such as by molding to have a perforated support means embedded within the module, and with a suitable bore for enabling the required fastening of the module to a furnace shell or the like. The system further includes a stud as part of the fastening means, said stud being passed through the bore and through an opening in the support means such that the stud can be readily welded to the furnace shell after the module has been placed against the shell. A locking means is locked into place on the free end of the stud, which end is located deep within the bore. A plug is fitted into the bore at the inner or "hot" face of the module, thereby to prevent corrosion of the fastening means; likewise, to preclude heat transfer from the interior of the furnace to the furnace shell.

2 Claims, 1 Drawing Sheet

REFRACTORY FIBER MODULE RETAINER SYSTEM

This application is a continuation of application Ser. No. 634,739, filed July 26, 1984, now abandoned which is a division, of application Ser. No. 320,388, filed Nov. 12, 1981 now abandoned.

BACKGROUND OF THE INVENTION

1. Field of the Invention

This invention relates to heat insulation for industrial furnaces and the like, and more particularly to a retainer system for simplifying the retention of refractory fiber modules as an insulating medium.

The use of refractory fiber for insulating purposes in the lining of industrial furnaces has grown very rapidly in the past several years. Formerly, the most common arrangement was to use blanket linings, but these are being replaced by so-called fiber modules of various shapes and constructions. Most of these modules are produced using blanket material cut into strips and formed into modules, most commonly sized at twelve inches by twelve inches and having various thicknesses from two inches to twelve inches.

2. Background Information

In order that the invention may be appreciated in its proper context, reference may be made to the following background material which is in the form of bulletins of various major manufacturers of heat insulating furnace linings:

1. Carborundum Co. bulletin on FIBERWALL TM furnace linings
2. Pyroblock ® bulletin
3. Babcock & Wilcox bulletin on KAOWOOL ® blanket lined furnaces In the first listed bulletin put out by the Carborundum Company, there is described an installation system for a furnace lining involving a ceramic fiber module constituted of layers of mineral wool block and thermal shock resistant ceramic material. A fastening means includes a stud on which the several linings or layers are impaled; a cup-shaped locking means engages the stud.

Another of the aforenoted bulletins describes a so-called "PYROBLOCK" ® system, involving a plurality of ceramic fiber strips bonded to an expanded metal substrate and including a special fastener. The installation procedure with this system includes welding of the fastening stud that is used to the furnace shell after the module as defined has been placed in position against the furnace shell.

The bulletin of Babcock and Wilcox describes the installation of blanket linings over a mineral wool base or substrate. A variety of fastening or anchoring devices are described; however, all of these provide that a nut or locking washer bears against the innermost layer; that is, the layer at the hot interior of the furnace or the like.

It will thus be appreciated that problems remain with respect to the mounting or fastening of blankets or modules of conventional construction to the outer shell of heat treating furnaces. Notably, considerable cost is involved in attempting to retain the lightweight fiber blanket materials utilized in forming a layered fiber module so that the module will be adequately supported mechanically.

It should also be noted that many of the conventional retaining methods as practiced require accurate layout of the furnace shell for prewelding of the anchoring or fastening devices; that is to say, the studs or similar devices that are deployed. It is apparent that such methods are relatively time consuming and costly.

Accordingly it is a primary object of the present invention to achieve firmness of support and security in the fastening or anchoring of refractory fiber modules, while significantly lowering the cost involved.

Another object is to simplify the installation procedure for such fiber modules by permitting the welding or otherwise securing of the fastening stud after the fiber module has been placed in position against the furnace shell.

Yet another object is to insure protection of the fastening or anchoring means from corrosion as a result of being exposed to the hot gases of the furnace; at the same time, substantially to prevent heat transfer from the furnace interior by way of the fastening stud to the furnace shell.

SUMMARY OF THE INVENTION

The above as well as other objects are implemented and fulfilled by the several features of the present invention. The primary feature resides in the provision of a unitary refractory fiber module in which a perforated support means is embedded. Due to the homogeneous rigid structural form for the module, there is inherently a much greater mechanical strength provided. This results from the fact that the fiber module is vacuum formed by well known molding techniques. Such vacuum molding techniques may be thoroughly appreciated by reference to U.S. Pat. Nos. 3,500,444 and 3,866,017. In order to mechanically fasten the module to the furnace shell, the aforenoted perforated support means is molded in situ, that is to say, is embedded within the vacuum formed module. This increases the area of support around a simple, commercially available, conventional fastening stud forming part of the system. This fastening stud can be either threaded or notched as desired.

A more specific feature of the invention further includes a central bore extending through the molded fiber module; that is to say, formed in the molding process or method so as to communicate with the perforated support means, such support means being preferably in the form of a perforated disc having a central opening located so as to correspond with the central bore.

As a result of the central bore communicating with the perforated disc, the fastening stud can—after the fiber module has been placed in position against the furnace shell—be extended through the bore and thereafter welded by a conventional stud welding gun. Because of the location of the perforated disc, that is, deep within the insulating fiber module, the fastening is accomplished such that the fastening means is completely protected, rather than being exposed to the ravages of the furnace heat with the consequence of severe deterioration.

A further specific feature of the invention resides in the provision of a vacuum formed plug of the same material as the module which insures the insulation of the fastening means so as to completely eliminate the deterioration problem. However, a further advantage provided by this feature is that the plug may be simply removed to expose the washer or other fastening device, so that the washer can be removed and the individual module can be easily replaced in the event that a module should become physically damaged.

Other and further objects, advantages and features of the present invention will be understood by reference to the following specification in conjunction with the annexed drawing, wherein like parts have been given like numbers.

DESCRIPTION OF PREFERRED EMBODIMENT

Figure 1:
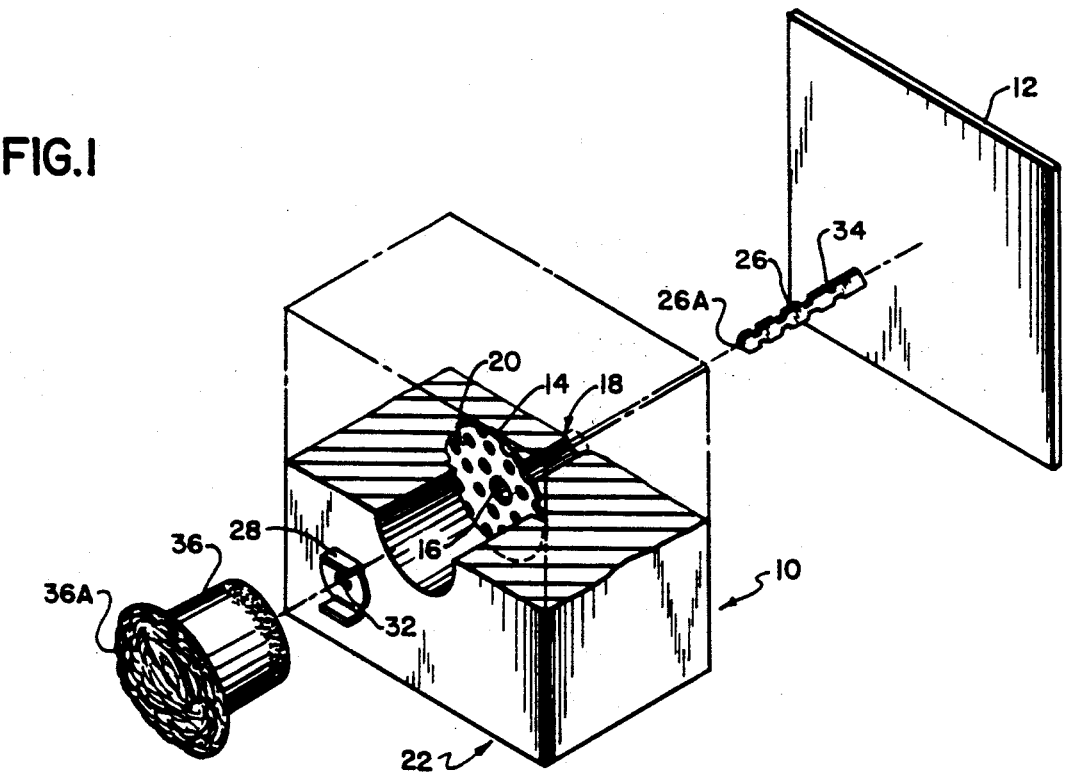
FIG. 1 is an exploded view of the several components constituting the refractory fiber module retainer system.

Referring now to the figures of the drawing, there will be seen in the exploded view of FIG. 1 the complete assemblage of components that make up the retainer system. The refractory fiber insulating module 10 is a unitary module constituted preferably of ceramic fibers such as alumina silica. This module 10 is produced by vacuum molding techniques and in its formation an inorganic binding agent is used. This results in an insulating material of approximately 13 pounds per cubic foot density which contrasts with the more conventional 6 to 8 pound per cubic foot blanket modules currently on the market.

It will be apparent that it is due to the homogeneous rigid structure thus formed that the module 10 has far greater inherent mechanical strength than modules made up of layers of conventional materials.

While the module per se has been produced heretofore, it has not been adapted to produce the results afforded by the present invention. Thus, in order to achieve efficiency and security in fastening the fiber module to the furnace shell 12, a portion of which is illustrated in the figures, a perforated support means 14 in the form of a disc having a central opening 16 is molded in situ as the module 10 is fabricated. At the same time, a bore 18 is created through the module 10 in the molding process.

The perforated support means 14 has sufficiently large openings 20 surrounding its center so as to permit the refractory fibers to be drawn into and around the openings, thereby to interlock with the metal grid and bind it tightly into the vacuum formed insulating module 10. The particular size and shape of the openings 20 in the grid or support means 14 are not critical, but must provide sufficient open area to allow the fibers to pass through and around the metal portions. It will be understood that support means 14 may be varied in shape as desired.

The support means 14 must be located a reasonable distance from the hot face 22 of the module 10 such that there will be a sufficient temperature drop due to the insulating quality of the refractory fiber. However, the support means 14 cannot be located so far away from the hot face 22 as to reduce the effectiveness of the support provided by the material behind it. Since these insulating modules are produced in various thicknesses from two inches to six inches in typical production, the grid or support means should be located approximately one half to two-thirds of the thickness from the hot face.

The fastening or anchoring means 24 is illustrated as including a stud 26 and a locking washer 28. These components are per se well known, and it will be appreciated that other similar components such as a threaded stud and a corresponding nut can likewise be employed for fastening purposes.

Figure 2:
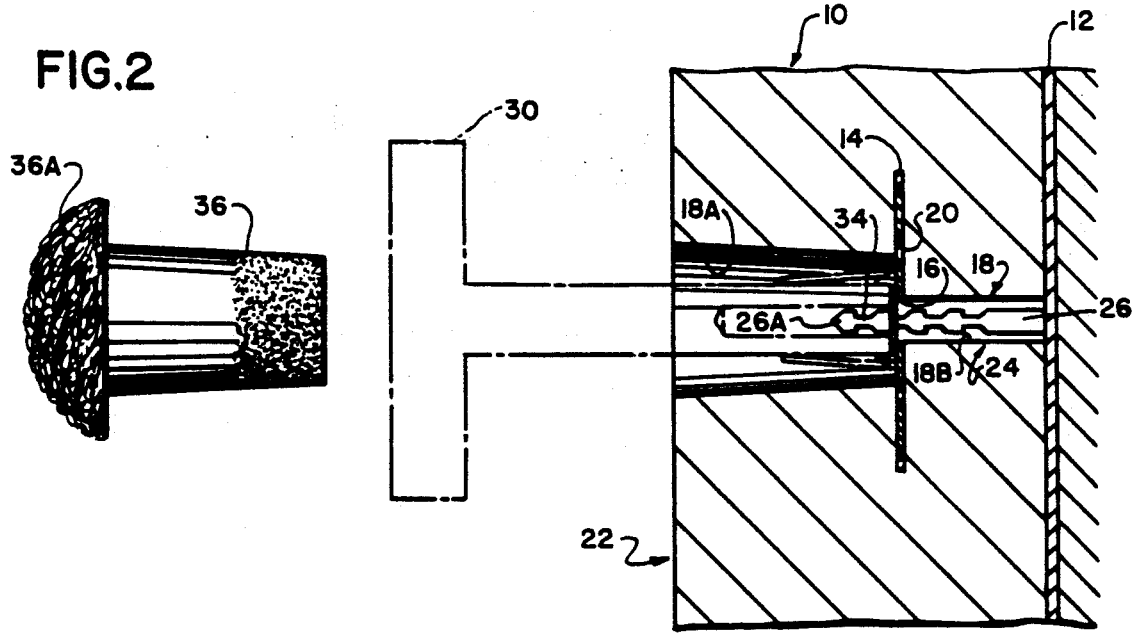
FIG. 2 is a side view in section, illustrating the fiber module in place, i.e. fastened to a furnace shell, being shown at the point where a locking washer is being tightened by a suitable tool before the plug, also shown, is inserted into the module.

As seen in FIG. 2 in phantom outline, a conventional tool 30 is deployed in order to move the locking washer 28 into its locked position. This washer includes a slotted opening 32 such that in one position the washer can be moved by the notches 34 in the stud 26. Once the locking washer is brought up to a point such that it bears against the support means 14 it is turned 90° so as to be held within the appropriate notch 34.

Once the fastening means has been secured, a plug 36, which is constituted of the same or similar material as the module 10, may be snugly fitted within the portion 18A of the bore. This bore portion 18A has a much greater diameter in this particular example than the remaining bore portion 18B at the other side of the support means 14. Of necessity, bore portion 18A is large enough to provide sufficient space for installing the locking washer 28, if this means is selected for fastening purposes.

It is preferred that the bore portion 18A which receives the plug 36 is of tapered construction to provide for positive sealing with suitable refractory cement, the taper being most effective from about 1° to 10°. The plug 36, likewise tapered, can also be vacuum formed, and is preferably produced with a cap 36A in the molding process. This cap is most effective in sealing the opening of bore portion 18A and provides additional insulation over the retaining stud 26 and washer 28. This cap also reduces shrink at the parting line. However, if desired this cap may be cut off to provide a smooth inner furnace wall.

It will be understood that the increased bearing or support area as provided by the present invention produces greater mechanical support for the fiber modules, especially for modules which are mounted to the roof of furnaces. By reason of the present invention, the modules 10 have sufficient strength to enable the roof to be insulated "flat", rather than having to provide the typical refractory brick arch construction.

It will have become apparent that by the construction of the present invention, the fastening or anchoring means 24 can be located deep within the fiber module 10 for complete protection of the fastening means. Moreover, the fastening means per se is conventional so that additional cost is not required for special washers or the like.

The present invention also provides the known advantage of post welding of the stud 26. Thus, in the installation procedure the fiber module 10 is brought up against the shell 12; then, a welding gun is clamped to the tip 26A of the stud. The stud 26 is inserted through the bore 18 and, of course, through the central openings 16 of the support means. A sufficient current is provided by the welding gun to effect welding of the stud to the shell 12.

While there has been shown and described what is considered at present to be the preferred embodiment of the present invention, it will be appreciated by those skilled in the art that modifications of such embodiment may be made. It is therefore desired that the invention not be limited to this embodiment, and it is intended to cover in the appended claims all such modifications as fall within the true spirit and scope of the invention.

I claim:

1. A method of forming a refractory fiber module retainer system comprising the steps of:

vacuum molding a rigid module of refractory fiber material, including embedding in-situ, during the vacuum molding of the module, a support means in the form of a thin perforated disk, such disk having a central opening for permitting a first element of a fastening means to pass therethrough, said disk further having perforations completely surrounding its central opening for permitting the refractory fibers to be drawn into and around the perforations, thereby to interlock with the support means and bind the support means tightly into said rigid module;

further including forming, during the vacuum molding of said rigid module, a bore extending entirely through said module, a portion of said bore immediately adjacent said central opening having a larger diameter than said opening to permit a second element of said fastening means, while engaging said first element, to contact a plane surface of said disk, the central opening of said disk being substantially concentric with the center of said bore.

2. A method as defined in claim 1, including the step of forming another portion of said bore to have a predetermined diameter and to extend through approximately one-third of the thickness of said module, and forming the bore with a further portion which is tapered and has a substantially larger diameter throughout, compared with the diameter of said another bore portion.

* * * * *